United States Patent [19]
McCue et al.

[11] Patent Number: 5,733,290
[45] Date of Patent: Mar. 31, 1998

[54] QUICK-RELEASE TIBIAL ALIGNMENT HANDLE

[75] Inventors: Diane F. McCue, Pocasset; Ernest Quintanilha, Norton, both of Mass.; Sarah Anne Wildgoose, Smithfield, R.I.; Dennis P. Colleran, Plainville; Timothy M. Flynn, Norton, both of Mass.

[73] Assignee: Johnson & Johnson Professional, Inc., Raynham, Mass.

[21] Appl. No.: 576,745

[22] Filed: Dec. 21, 1995

[51] Int. Cl.⁶ ....................................... A61F 5/00
[52] U.S. Cl. ................................................ 606/86
[58] Field of Search .................... 606/85, 86, 87, 606/88, 96; 623/20

[56] References Cited

U.S. PATENT DOCUMENTS

| | | | |
|---|---|---|---|
| 3,798,706 | 3/1974 | Wolfson et al. | 16/114 A |
| 4,825,857 | 5/1989 | Kenna | 606/88 |
| 4,921,493 | 5/1990 | Webb, Jr. et al. | 606/85 |
| 5,089,003 | 2/1992 | Fallin et al. | 606/85 |
| 5,116,338 | 5/1992 | Poggie et al. | 606/90 |
| 5,261,915 | 11/1993 | Durlacher et al. | 606/85 |
| 5,433,471 | 8/1995 | Swajger | 606/99 |
| 5,499,984 | 3/1996 | Steiner et al. | 606/80 |
| 5,499,985 | 3/1996 | Hein et al. | 606/99 |

FOREIGN PATENT DOCUMENTS 0 474 320 A1  3/1992  European Pat. Off.  ........ A61F 2/46

Primary Examiner—Michael Buiz
Assistant Examiner—David O. Reip
Attorney, Agent, or Firm—Susan M. Schmitt

[57] ABSTRACT

A quick-release alignment handle system is provided including a quick release alignment handle with an attachable, releasable locking mechanism for attaching the handle to a tibial tray trial component of a surgical instrument system for implanting artificial knees.

7 Claims, 5 Drawing Sheets

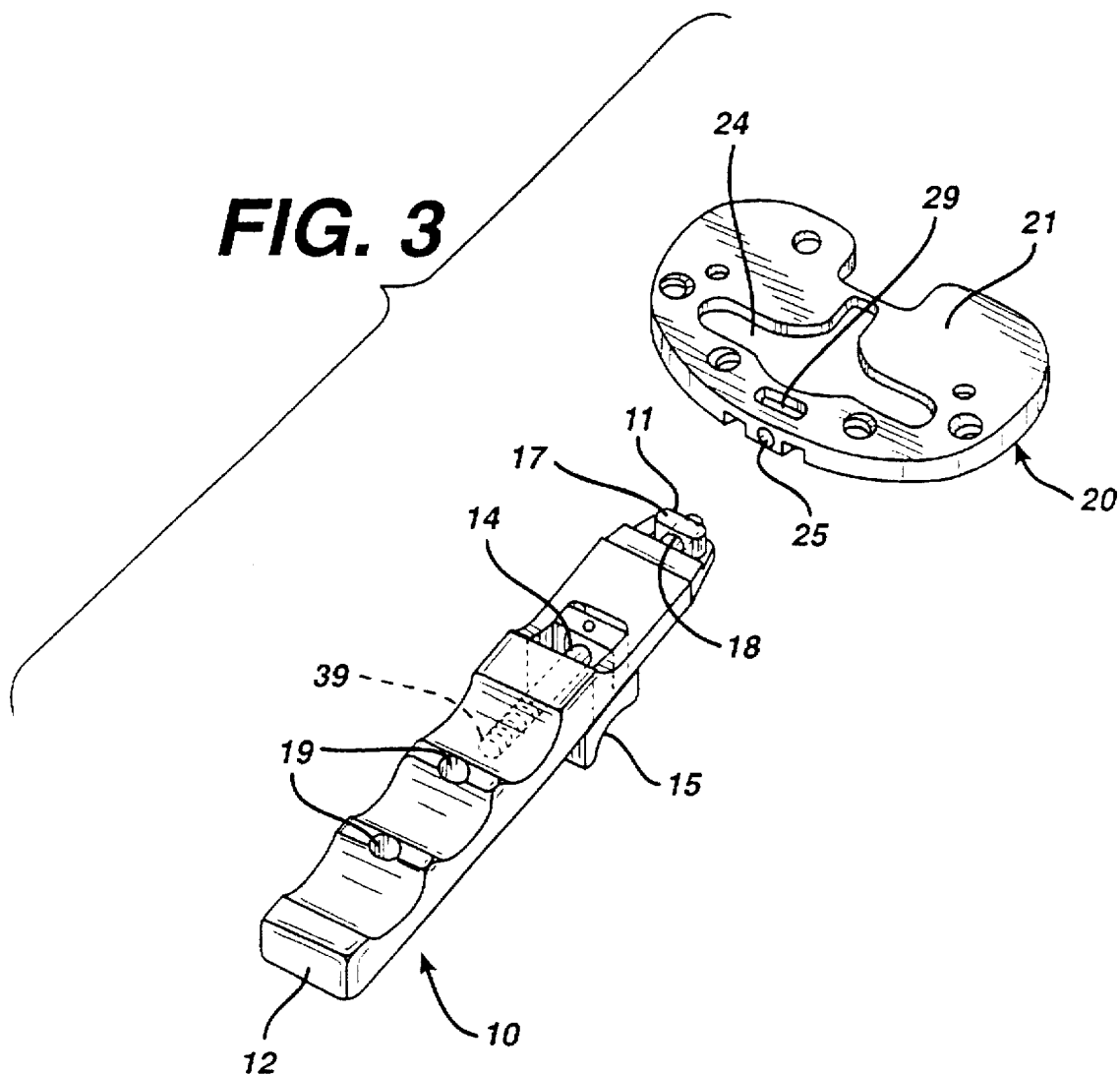

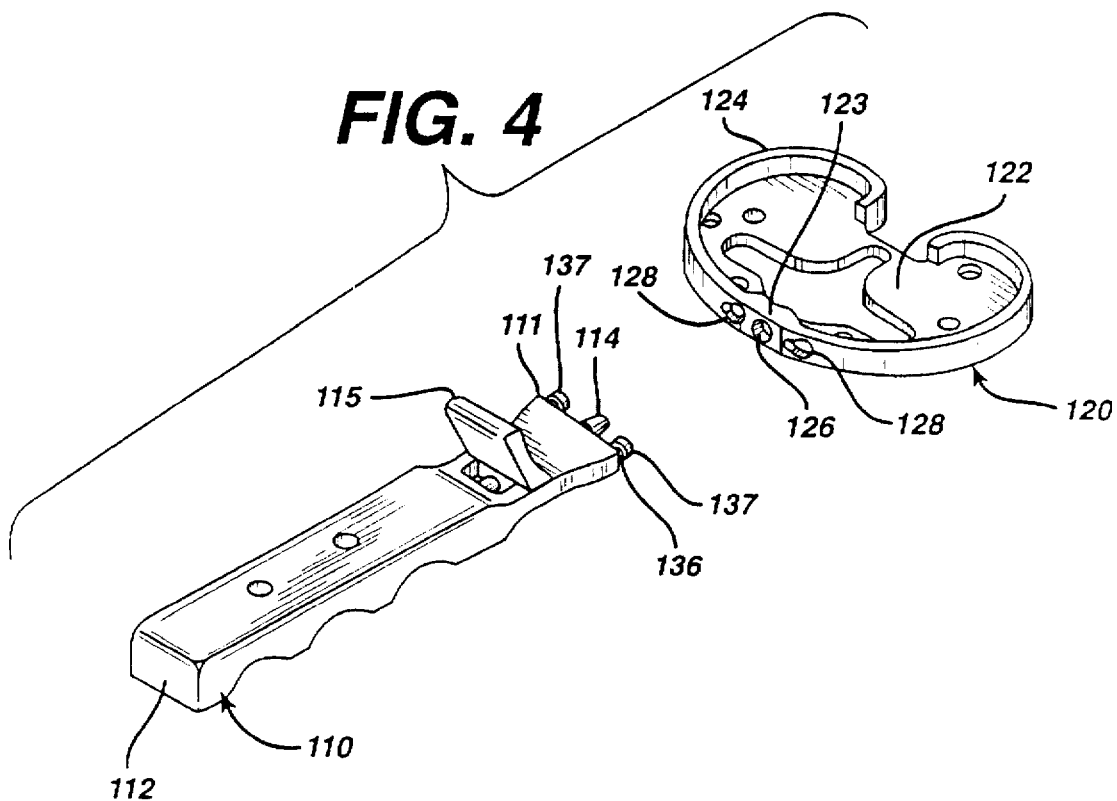
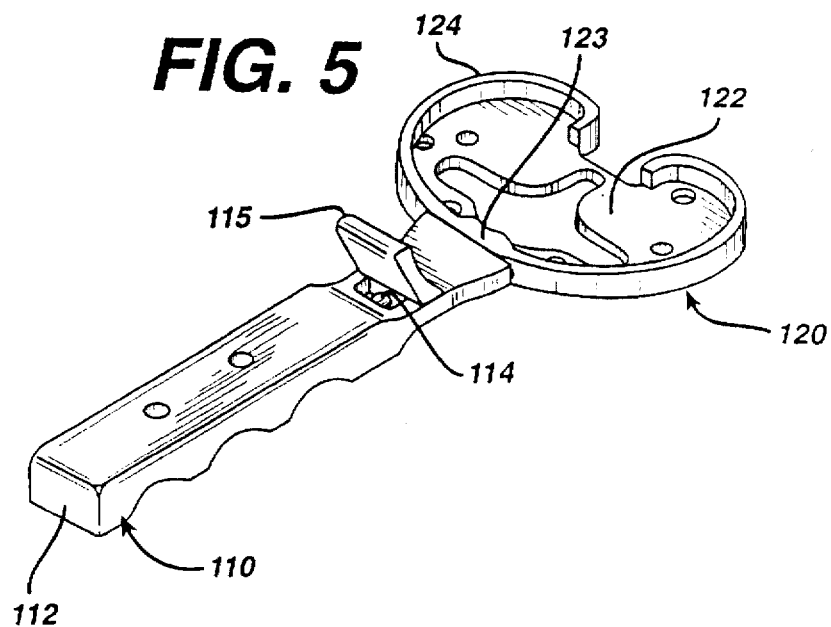

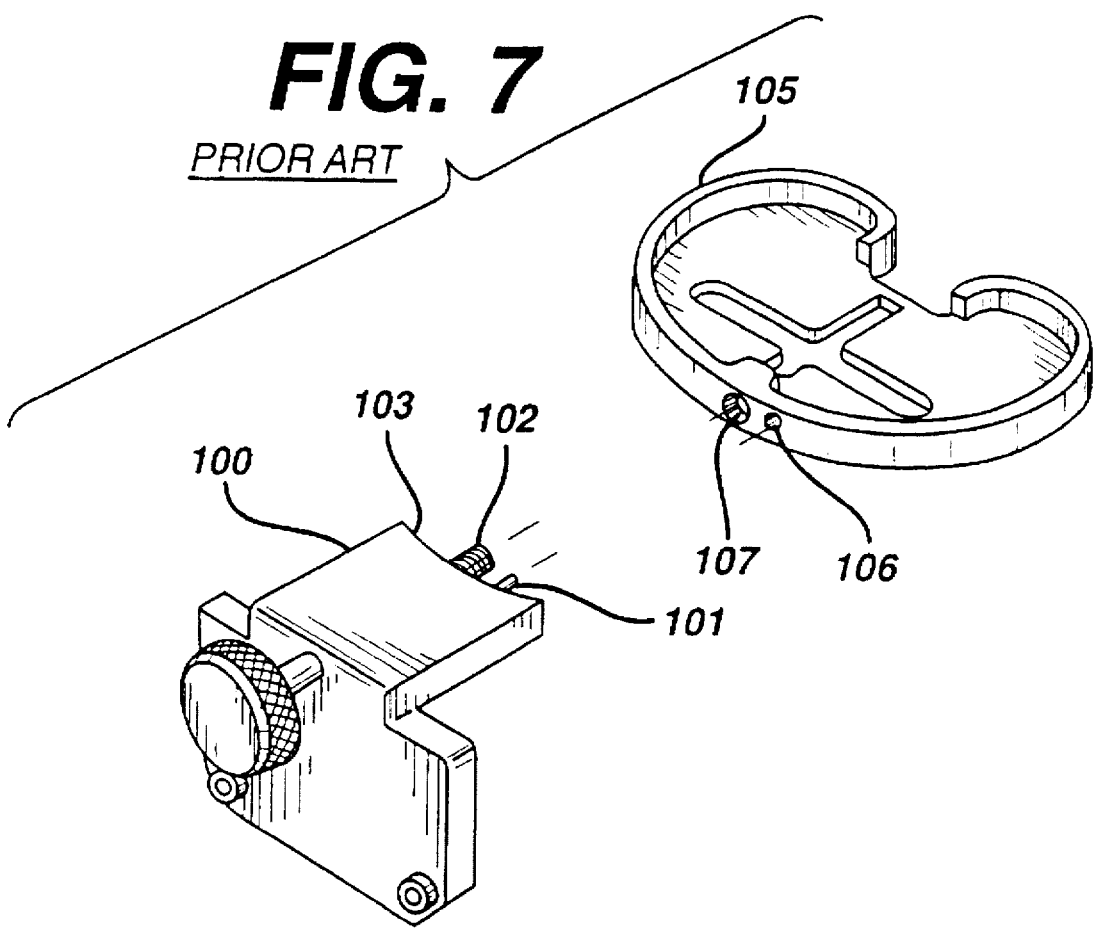

QUICK-RELEASE TIBIAL ALIGNMENT HANDLE

FIELD OF THE INVENTION

The present invention relates to a handle for aligning a tibial tray trial used at various times during a knee replacement surgical procedure.

BACKGROUND OF THE INVENTION

During knee replacement surgery tibial trials are used to assist a surgeon in preparing the tibial surface for implantation of the tibial portion of the artificial knee. A surgeon uses a tibial tray trial to determine the tibial implant size, to make the appropriate cuts and reams in the bone, and to ensure a proper alignment and tibial component thickness prior to implanting the tibial components.

Such a procedure typically entails making an initial tibial plateau cut on the proximal tibial portion of the knee; determining a preferred size tray trial (and ultimately tray implants); placing the selected tray trial over the tibial surface; performing a trial reduction to ensure proper tibial component thickness and alignment; removing the tray trial to attach a punch guide; placing a punch guide and tray trial on the resected tibial surface knee; and cutting or reaming the tibial bone through openings in the punch guide and tray trial to prepare it to receive a stem or keel of the tibial implant. During this procedure it is frequently necessary for the surgeon to remove the tray trial and replace the tray trial, as well as to remove the handle holding the tray trial so that the knee alignment and tibial component thickness may be evaluated.

In the existing art, a tibial alignment handle is attached by way of a screw to the tibial tray trial. A screw type handle can be cumbersome to attach. Screws have a tendency to be weaker and/or break. Furthermore, the threads for attachment in screw type devices may have a tendency to gaul, bind and fail.

Accordingly, it is desirable to have a tibial tray trial and an alignment handle system which enables quick and secure attachment or removal of the handle from the tray trial.

SUMMARY OF THE INVENTION

The present invention provides a tibial alignment handle with a quick release attachment mechanism. In a preferred embodiment, the quick release mechanism comprises a captive spring-loaded sliding bolt which engages a mating part built into the tray trial. The sliding bolt may be retracted by a release button located on the alignment handle so that the button may be engaged by the thumb or the finger of a user to attach or detach the alignment from a mating component. Another feature of the preferred embodiment includes a mechanical lock between the handle and mating component that prevents rotation between the components.

DETAILED DESCRIPTION OF THE DRAWINGS

FIG. 3 illustrates an exploded perspective view from the bottom side of the system illustrated in FIG. 1;

FIG. 4 illustrates an exploded perspective view of the top of an alignment handle and tibial tray trial locking system of the present invention;

FIG. 5 illustrates an assembled perspective view of the system of FIG. 4 with the tibial tray trial and alignment handle attached;

FIG. 7 illustrates a locking mechanism of the prior art.

DETAILED DESCRIPTION OF THE INVENTION

Figure 1:
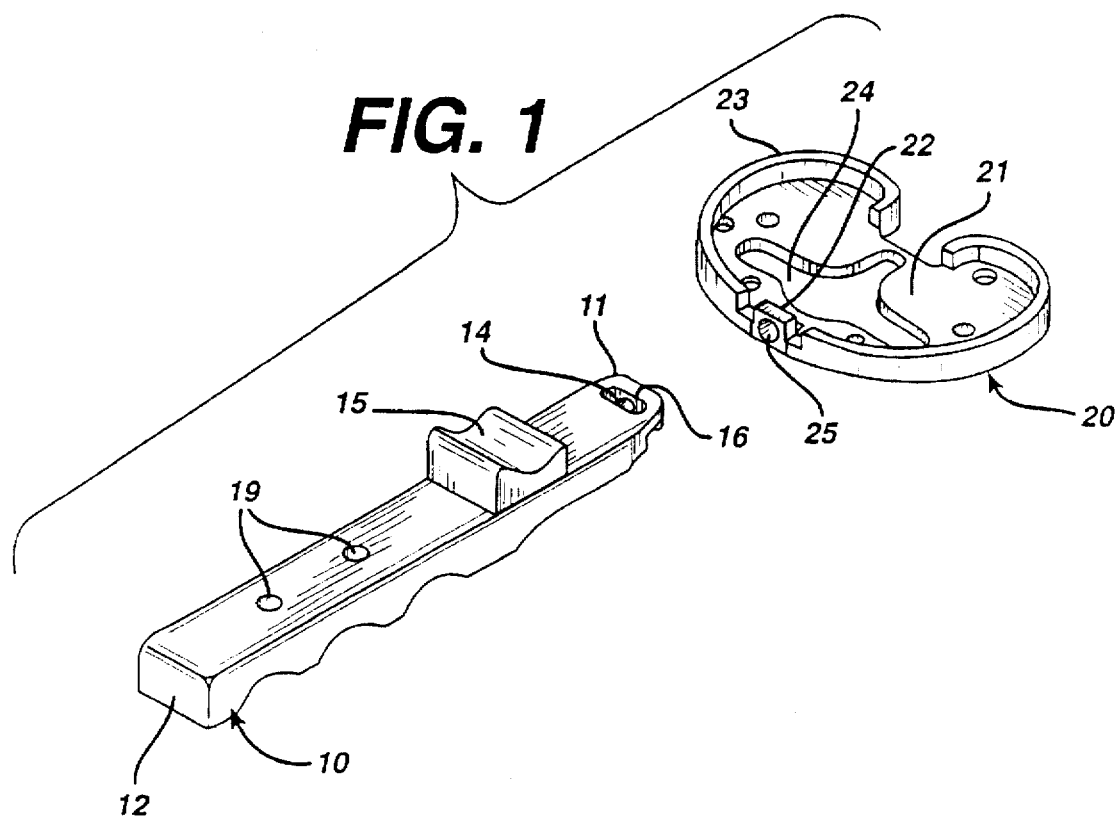
FIG. 1 illustrates an exploded perspective view of the top of an alignment handle and tibial tray trial locking system of the present invention.

Referring to FIG. 7, a screw type device of the prior art is illustrated. The handle 100 includes a universal 101 and a thumb screw 102 located on the distal end 103 of the alignment handle 100. The tray trial 105 comprises a threaded portion 107 and a hole 106 for receiving the universal 101. In use, the alignment handle (or tray trial) is held in one hand while a second hand is used to insert the universal 101 into the hole 106 and screw the thumb screw 102 into the threaded portion 107.

Figure 2:
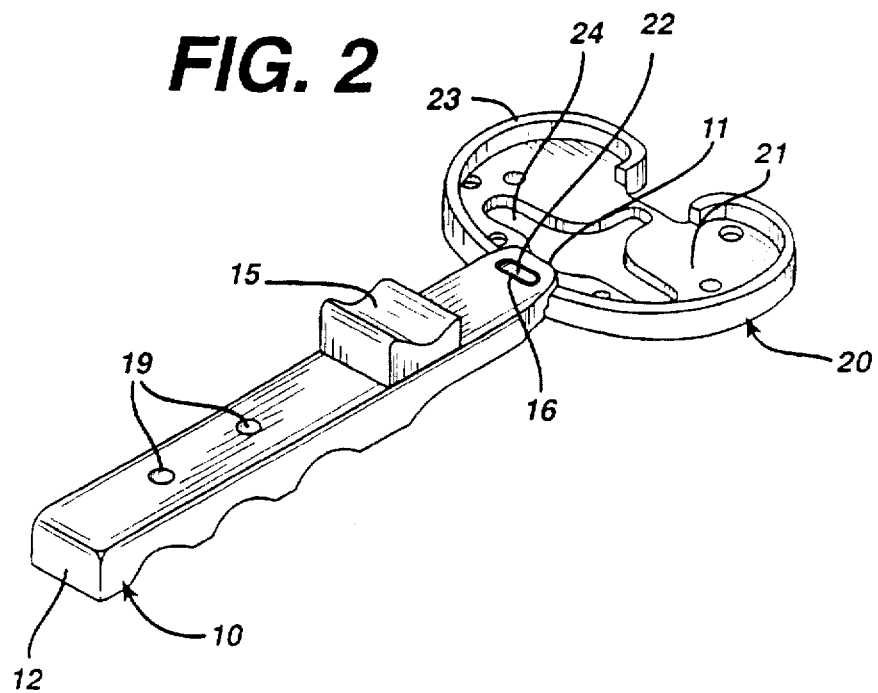
FIG. 2 illustrates an assembled perspective view of the system of FIG. 2 with the tibial tray trial and alignment handle attached.

Referring now to FIGS. 1–3, a quick release system of one embodiment of the present invention is illustrated. The system includes an alignment handle 10 and a tibial tray trial 20.

An alignment handle 10 is illustrated having a handle end 12 and a connecting end 11. The alignment handle 10 includes a release button 15 slidable in a direction from the connecting end to the handle end, i.e., posterior to anterior, and visa versa, and spring-biased in an anterior to posterior direction. The button 15 is coupled to a sliding bolt 14 which is captive, i.e., contained within the alignment handle 10. The bolt 14 is spring-loaded in a direction from anterior to posterior with spring 39. The connecting end 11 of the alignment handle 10 comprises an opening 16 arranged to received a mating portion 22 on the tibial tray trial 20. The connecting end 11 further comprises a mechanical lock portion 17 posterior of said opening 16, arranged to coupled and lock with the mating portion 22 of the tibial tray trial 20. The bolt 14 extends to the connecting end 11, through the opening 16 and through a hole 18 in the mechanical locking portion 17. When the release button 15 is retracted in a proximal direction, the bolt 14 is retracted to a position anterior of the opening 16, allowing the opening 16 to receive the mating portion 22 of the trial 20.

The tibial tray trial 20 comprises a plate portion 21, a mating portion 22, a rim 23 around the outer circumference of the plate 21, and a punch guide opening 24 formed in the tibial tray trial plate 21. The mating portion 22 includes a hole 25 for receiving the bolt 14 of the alignment handle 10. The plate 21 includes a slot 29 for receiving the mechanical locking portion 17 of the alignment handle 10.

In use, a user controls the attachment and detachment of the alignment handle 10 using the release button 15. The release button 15 is pulled in an anterior direction which retracts the bolt 14 into the alignment handle 10. The mechanical locking portion 17 fits into the slot 29 of the trial 20 and the mating portion 22 fits within the opening 16 at the proximal end 11 of the alignment handle 10. The user may then release the release button 15 and the spring bias of the bolt 14 moves the bolt 14 proximally through the hole 25 in the mating portion 22 and into the hole 18 in the mechanical locking portion 17 at the proximal end 11 of the alignment handle 10.

Alignment handle 10 further comprises holes 19 for receiving alignment rods (not shown) used to check alignment of the tibial tray with the femur.

As described previously, tibial surface is cut so that the tibial tray trial 20 will rest on a flat surface. Then; the tibial tray trial 20 is used as a template to select the appropriate size tibial prosthesis for implantation. The alignment handle 10 is used to manipulate the tray trial. Various sizes of tray trials are attached and removed from the alignment handle to select a trial closely matching the tibial plateau. At any time during the procedure the surgeon may use the alignment handle 10 to place the tray trial 20 on or remove it from the tibia. The surgeon may do this with one hand leaving the other hand free.

Once the size is selected, the trial is placed to rest on the bone. A tibial trial insert (not shown) is inserted within the rim 23 of tray trial 20. The insert is used to determine the tibial implant thickness and provide a surface with which a femoral trial, indicative of the implant, will interact. Various trial inserts are tried to select the one of an appropriate thickness. Alignment rods may be inserted into the holes 19 and used to check the alignment of the tray 20 with the femoral portion of the implant. The surgeon may then remove the alignment handle, replace the patella portion and check the alignment and movement of the trials. Once it has been determined that the trial is appropriately sized and fitted and has been appropriately placed on the tibia, the alignment handle 10 and trial insert are removed. The surgeon will also remove the femoral trial and attach a punch guide to the tray trial. In order to prepare the tibia for the tibial implant, a punch or reaming device is then inserted through a punch guide (not shown) which is placed over the punch guide opening 24.

Figure 6:
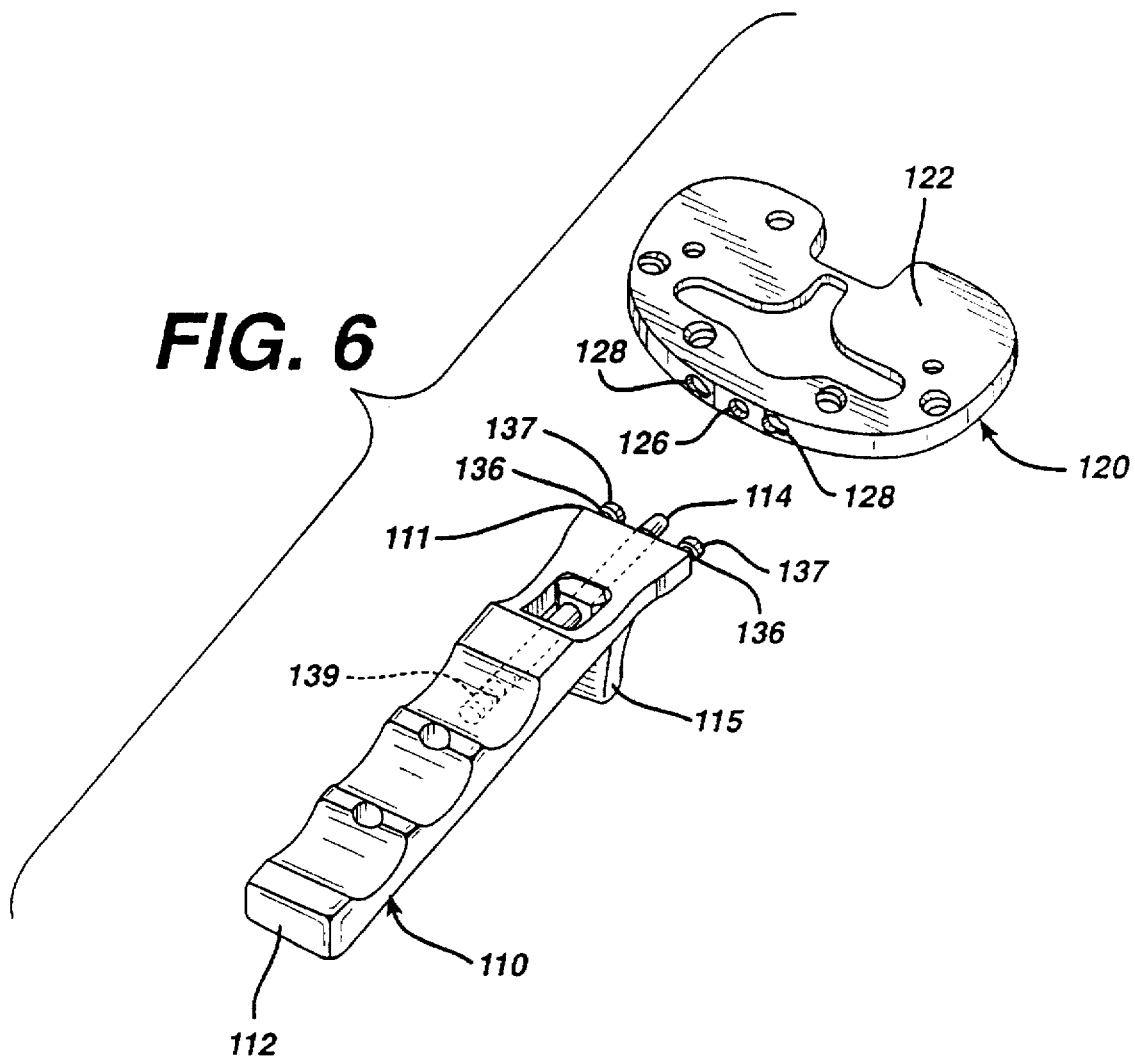
FIG. 6 illustrates an exploded perspective view from the bottom side of the system illustrated in FIG. 4.

Referring now to FIGS. 4-6, an alternative embodiment of the present invention is illustrated. The system comprises an alignment handle 110 and a tibial tray trial 120.

The alignment handle 110 is illustrated having a handle end 112 and a connecting end 111. The alignment handle 110 includes a release button 115 slidable in a direction from the connecting end to the handle end, i.e., posterior to anterior, and visa versa. The button 115 is coupled to a sliding bolt 114 which is captive, i.e., contained within the alignment handle 110. The bolt 114 is spring-loaded in a direction from anterior to posterior with spring 139. The connecting end 111 of the handle 110 comprises connecting bolts 136 having cylindrical heads 137 on the end of the bolts 136. The heads 137 have a greater circumference than the circumference of the bolts 136.

The tibial tray trial 120 comprises a plate portion 122, a rim 124 around the outer circumference of the plate 122, a mating portion 123 of the rim 124.

The mating portion 123 includes a hole 126 for receiving a sliding bolt 114 of the handle 110 and openings 128 for receiving connecting bolts 136 of the handle 110. Openings 126, 128 extend through the rim 124 of the mating portion 123. Openings 128 each include a first portion on one transverse side of the opening 128 having a first radius and a second portion on the opposite transverse side having a second radius smaller than the first radius.

The bolt 114 extends from the connecting end 111 when the button 115 is extended, and retracts into the handle end 112 when the button 115 is retracted. The bolts 136 are slid into openings 128, the first radii of the openings 128 being large enough to accommodate the larger circumference of heads 137 of the bolts 136 which, when, inserted into the openings 128, extend beyond rim 124. The handle 110 is then moved in a direction towards the second portion of the opening 128 into a locked position. The second radii are too small to permit passage of the larger circumference heads 137 but large enough to receive the smaller circumference bolts 136.

In use, a user controls the attachment and detachment of the handle 110 to the tray trial 120, using the release button 115. The release button 115 is pulled in an anterior direction which retracts the bolt 114 into the handle 110. The heads 137 of the bolts 136 on the distal end 111 of the handle 110 are inserted into openings 128 and moved to the locked position as described above. The bolt 114 is aligned with the opening 126 when the handle 110 is in the second or locked position. Thus, when the user releases the release button 131, the spring 139 causes the bolt 114 to move through the hole 126 in the mating portion 123. The locked bolt 114 prevents side to side movement of the handle 110 and the heads 137 prevent the bolts 136 from pulling out of holes 128.

The quick-release and locking mechanism of the second embodiment is used in a manner similar to that described above with respect to the first embodiment.

Although the present invention is described with respect to particular embodiments, and uses, numerous variations or equivalents are possible without taking away from the spirit or the scope of the claimed invention.

We claim:

1. A tibial tray alignment handle for use in prosthetic knee implantation surgery, said handle comprising:
    a body having a connecting end portion, said connecting end portion
        comprising a locking member having at least one tab portion extending from said body and arranged to engage into an opening in a tibial tray trial to prevent tray trial movement away from said body;
    a connecting member located at said connecting end portion, said connecting end portion having a first position whereby said connecting member is positioned to couple with a mating portion of a tibial tray trial, and a second position whereby said connecting member is positioned to release from the mating portion of the tibial tray trial, wherein said connecting member is spring biased towards said first position; and
    a hand actuable quick-release button located on said body and coupled to said connecting member, said button moveable to move said connecting member from said first position to said second position.

2. The handle of claim 1 wherein said connecting member comprises:
    a sliding bolt extendable from said connecting end portion and retractable in a direction towards said body to said second position; and
    a spring, biasing said bolt towards said first position in a direction extending from said body.

3. A tibial tray trial alignment handle system comprising:
    a tray trial comprising a distal portion for interfacing with a tibial portion of a knee joint, a proximal portion, and a wall connecting said proximal portion and said distal portion, said wall having an anterior portion, and a mating portion located on said anterior portion of said trial; and
    an alignment handle comprising:
        a body having a connecting end portion;
        a connecting member located at said connecting end portion, said connecting member having a first position whereby said connecting member is coupled with the mating portion of the tibial tray trial, and a second position whereby said connecting member is released from the mating portion of the tibial tray trial, wherein said connecting member is spring biased towards said first position; and a hand actuable quick-release button located on said body and coupled to said connecting member, said button moveable to move said connecting member from said first position to said second position.

4. The system of claim 3 wherein said connecting member further comprises:
   a sliding bolt extending from said connecting end portion and retractable in a direction towards said body to said second position; and
   a spring, biasing said bolt towards said first position in a direction extending said bolt from said body; and
   wherein said mating portion of said tray trial comprises:
   an opening for receiving said bolt.

5. The system of claim 4 wherein said connecting member further comprises:
   a locking member arranged to engage with the tray trial to prevent tray trial movement away from said sliding bolt.

6. The system of claim 5 wherein said locking member comprises:
   a locking bolt having a first diameter, and
   a head portion on the end of the locking bolt having a second diameter larger than said first diameter; and
   wherein said mating portion further comprises:
   an opening for receiving said head and said locking bolt, said opening having a first portion with a first diameter large enough to accommodate said first diameter of said bolt but too small to accommodate the second diameter of said head portion, and said opening having a second portion having a second diameter large enough to accommodate said head portion.
   wherein said sliding bolt is aligned with said opening for receiving said sliding bolt when said locking bolt is received by said first portion of said opening for receiving said head and said locking bolt.

7. The system of claim 4 wherein said locking member comprises:
   a first surface,
   wherein said tray trial comprises a second surface, and
   wherein said first and second surfaces are arranged to engage to prevent said handle from moving from said tray trial when said sliding bolt is inserted into said opening for receiving sliding bolt.

* * * * *